(12) United States Patent
Lee et al.

(10) Patent No.: US 10,556,859 B2
(45) Date of Patent: *Feb. 11, 2020

(54) PHTHALONITRILE COMPOUND

(71) Applicant: LG CHEM, LTD., Seoul (KR)

(72) Inventors: Seung Hee Lee, Daejeon (KR); Sang Woo Kim, Daejeon (KR); Ki Ho Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 68 days.

This patent is subject to a terminal disclaimer.

(21) Appl. No.: 15/575,744

(22) PCT Filed: May 20, 2016

(86) PCT No.: PCT/KR2016/005370
§ 371 (c)(1),
(2) Date: Nov. 20, 2017

(87) PCT Pub. No.: WO2016/190621
PCT Pub. Date: Dec. 1, 2016

(65) Prior Publication Data
US 2018/0118666 A1    May 3, 2018

(30) Foreign Application Priority Data

May 22, 2015    (KR) ........................ 10-2015-0071800

(51) Int. Cl.
| | | |
|---|---|---|
| *C08G 73/06* | (2006.01) | |
| *C07C 255/51* | (2006.01) | |
| *C08K 3/00* | (2018.01) | |
| *C08G 73/00* | (2006.01) | |
| *C07C 255/54* | (2006.01) | |
| *C08G 73/02* | (2006.01) | |
| *C08K 3/22* | (2006.01) | |
| *C08K 3/28* | (2006.01) | |

(52) U.S. Cl.
CPC .......... *C07C 255/51* (2013.01); *C07C 255/54* (2013.01); *C08G 73/00* (2013.01); *C08G 73/024* (2013.01); *C08G 73/0644* (2013.01); *C08K 3/00* (2013.01); *C08K 3/22* (2013.01); *C08K 3/28* (2013.01)

(58) Field of Classification Search
CPC ..... C07C 255/51; C07C 255/54; C08G 73/00; C08G 73/024; C08G 73/0644; C08K 3/00; C08K 3/22; C08K 3/28
See application file for complete search history.

(56) References Cited

U.S. PATENT DOCUMENTS

| 4,408,035 A | 10/1983 | Keller |
| 5,965,268 A | 10/1999 | Sastri et al. |

FOREIGN PATENT DOCUMENTS

| EP | 0413415 A1 | 6/1990 |
| JP | 47-16428 A | 9/1972 |
| JP | 64-51436 A | 2/1989 |
| JP | 0341050 A | 2/1991 |
| JP | 2002-519277 A | 7/2002 |
| KR | 100558158 B1 | 4/2001 |
| WO | 9918145 A1 | 4/1999 |

OTHER PUBLICATIONS

Eastmond, et al: "A Comparison of Poly(ether imide)s with 3-Phthalimide and 4-Phthalimide Units: Synthesis Characterization, and Physical Properties", American Chemical Society, Macromolecules, vol. 39, 2006, pp. 7534-7548.
Liaw, et al.: "Synthesis and Characterization of New Highly Organosoluble Poly(ether imide)s Based on 3,3', 5,5'-Tetramethyl-2,2-bis[4-(4-dicarboxyphenoxy)phenyl]propane Dianhydride", Journal of Applied Polymer Science: Part A: Polymer Chemistry, vol. 40, 2002, pp. 2556-2563.
Geoffrey C. Eastmond, et al., Influence of Change in Ether Structure on the Low Temperature Dielectric Relaxation of Some Poly(ether imide), Journal of Applied Polymer Science, 2014, vol. 131, pp. 41191 (1-10).
G. C. Eastmond, et al., Poly(ether imide)s with hindering substituents in the anhydride moiety: synthesis, properties and gas permeabilities, 1994, vol. 35(19), pp. 4215-4227.

*Primary Examiner* — Edward J Cain
(74) *Attorney, Agent, or Firm* — Dentons US LLP

(57) ABSTRACT

The present application relates to a novel phthalonitrile compound and a use thereof. The phthalonitrile compound has a novel structure and can exhibit excellent effects in a use known for which a phthalonitrile compound can be applied. The use of the phthalonitrile compound can be exemplified by a material or a precursor such as a phthalonitrile resin, a phthalonitrile dye, a fluorescent whitening agent, a photographic sensitizer, or an acid anhydride.

15 Claims, 2 Drawing Sheets

[Figure 1]
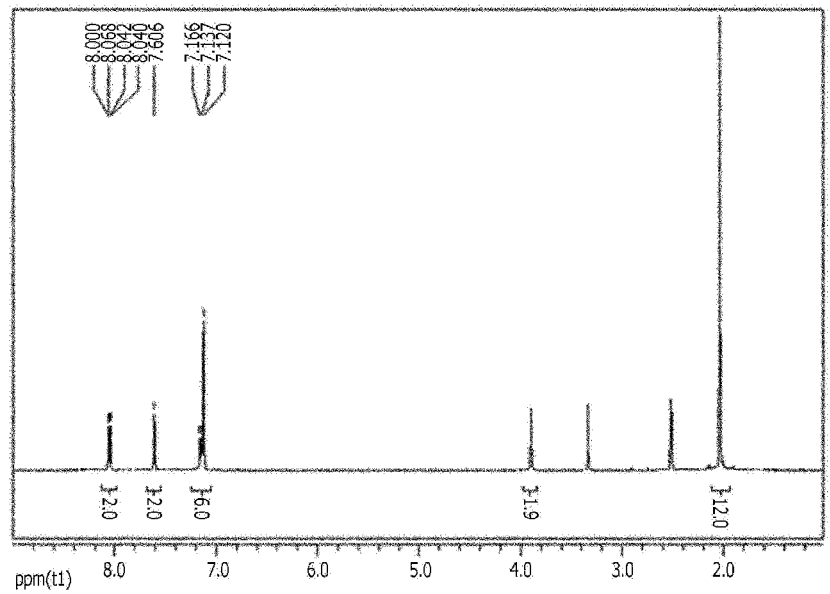
[Figure 2]
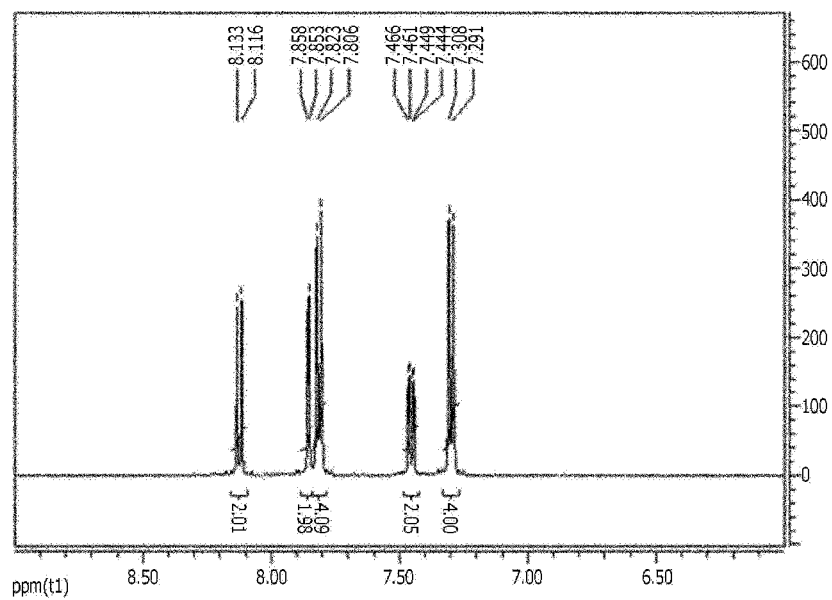

[Figure 3]
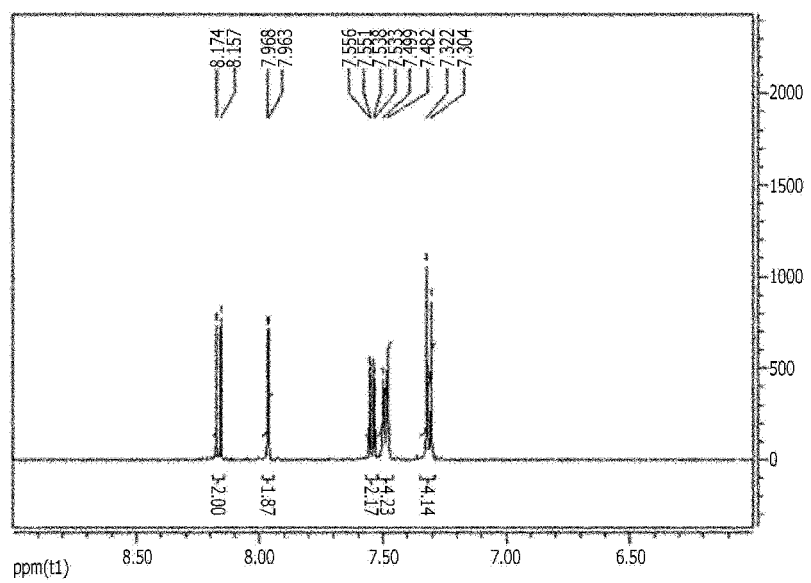

PHTHALONITRILE COMPOUND

This application is a National Stage Application of International Application No. PCT/KR2016/005370, filed May 20, 2016, and claims the benefit of Korean Patent Application No. 10-2015-0071800, filed May 22, 2015, contents of which are incorporated herein by reference in their entirety for all purposes as if fully set forth below.

TECHNICAL FIELD

The present application claims the benefit of priority based on Korean Patent Application No. 10-2015-0071800 filed on May 22, 2015, the disclosure of which is herein incorporated by reference in its entirety.

The present application relates to a phthalonitrile compound, a phthalonitrile resin, a polymerizable composition, a prepolymer, a composite, a precursor thereof, and a production method and use thereof.

BACKGROUND ART

Phthalonitrile can be used in various applications. For example, a composite formed by impregnating a resin (phthalonitrile resin) prepared using phthalonitrile as a monomer into a filler such as glass fiber or carbon fiber can be used as a material for automobiles, airplanes or ships. The process for producing the composite may include, for example, a process of mixing a mixture of phthalonitrile and a curing agent or a prepolymer formed by the reaction of the mixture with a filler and then curing the mixture (see, for example, Patent Document 1). In order for the composite preparation to be effective, it is required that the polymerizable composition or the prepolymer has appropriate fusibility and fluidity and a so-called process window is wide.

The other use of phthalonitrile compounds may include a use as precursors of phthalocyanine dyes. For example, a phthalonitrile compound may be compounded with a metal to be applied as a pigment.

The phthalonitrile compound can be also applied as a precursor of a fluorescent brightener or a photographic sensitizer or a precursor of an acid anhydride, and the like. For example, the phthalonitrile compound can be converted to an acid anhydride via an appropriate oxidation process and dehydration process, and such an acid anhydride can be also used as a precursor of polyamic acid or polyimide, and the like.

Prior Art Document

Patent Document (Patent Document 1) Korean Patent No. 0558158

DISCLOSURE

Technical Problem

The present application provides a novel phthalonitrile compound and a use thereof. The use of the compound may include most applications known that phthalonitrile compounds may be applied to, and as examples thereof, precursors or raw materials of phthalonitrile resins, polymerizable compositions, prepolymers, composites, pigments, fluorescent brighteners, photo sensitizers or acid anhydrides can be exemplified.

Technical Solution

The present application relates to a phthalonitrile compound. The compound may be represented by Formula 1 below.

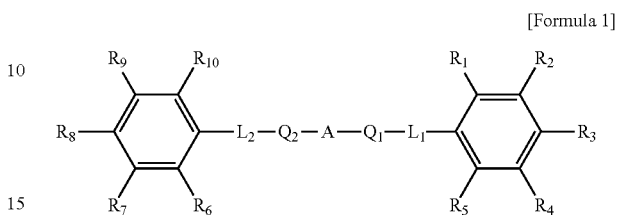

[Formula 1]

In Formula 1, A is an alkylene group or an alkylidene group having 1 to 20 carbon atoms, $Q_1$ and $Q_2$ are an aromatic divalent radical substituted with at least one alkyl group, $L_1$ and $L_2$ are each independently an alkylene group, an alkylidene group, an oxygen atom or a sulfur atom, $R_1$ to $R_{10}$ are each independently hydrogen, an alkyl group, an alkoxy group, an aryl group or a cyano group, provided that at least two of $R_1$ to $R_5$ are a cyano group and at least two of $R_6$ to $R_{10}$ are a cyano group.

In the present application, the term alkylene group or alkylidene group may be an alkylene group having 1 to 20 carbon atoms, 1 to 16 carbon atoms, 1 to 12 carbon atoms, 1 to 8 carbon atoms or 1 to 4 carbon atoms, unless otherwise specified. The alkylene group may be linear, branched or cyclic and may optionally be substituted with one or more substituents.

In the present application, the term alkyl group or alkoxy group may be an alkyl group or an alkoxy group, having 1 to 20 carbon atoms, 1 to 16 carbon atoms, 1 to 12 carbon atoms, 1 to 8 carbon atoms or 1 to 4 carbon atoms, unless otherwise specified. The alkyl group or the alkoxy group may be linear, branched or cyclic and may optionally be substituted with one or more substituents.

In the present application, the term aryl group may mean a monovalent radical derived from benzene, a benzene-containing compound or any one derivative of the foregoing, unless otherwise specified. Here, as the benzene-containing compound, a compound having a structure that two or more benzene rings are each condensed while sharing two carbon atoms, or linked by an appropriate linker, can be exemplified. The aromatic divalent radical may contain, for example, 6 to 25, 6 to 20, 6 to 15 or 6 to 12 carbon atoms and may optionally be substituted with one or more substituents.

In the present application, the term aromatic divalent radical may mean a divalent radical derived from benzene, a benzene-containing compound or any one derivative of the foregoing, unless otherwise specified. Here, as the benzene-containing compound, a compound having a structure that two or more benzene rings are each condensed while sharing two carbon atoms, or linked by an appropriate linker, can be exemplified. The aromatic divalent radical may contain, for example, 6 to 25, 6 to 20, 6 to 15 or 6 to 12 carbon atoms and may optionally be substituted with one or more substituents. In the present application, the term divalent radical or formation of radical may mean a state where the benzene, the benzene-containing compound or the derivative forms a covalent bond with other substituents, for example, A, L1 and/or L2 in Formula 1. Thus, in the present application, the term divalent radical may mean the case where two covalent bonds are present.

As the substituent with which the alkyl group, alkoxy group, aryl group, aromatic radical, alkylene group or alkylidene group in the present application may be optionally substituted, halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkoxy group or an aryl group can be exemplified, but is not limited thereto.

In the compound of Formula 1, $Q_1$ and $Q_2$ are each an aromatic divalent radical, provided that the aromatic divalent radical is substituted with at least one alkyl group.

In one example, the aromatic radical may be a radical derived from an aromatic compound derived from any one aromatic compound of Formulas 2 to 4 below.

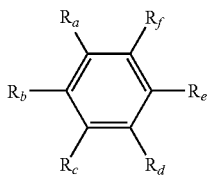

[Formula 2]

When the radical formed by Formula 2 is $Q_1$ in Formula 1, two of $R_a$ to $R_f$ in Formula 2 form a covalent bond, provided that any one of the substituents forming the covalent bond may form a covalent bond with $L_1$ in Formula 1 and the other may form a covalent bond with A in Formula 1, and when the radical is $Q_2$ in Formula 1, two of $R_a$ to $R_f$ in Formula 2 form a covalent bond, provided that any one of the substituents forming the covalent bond may form a covalent bond with $L_2$ in Formula 1 and the other may form a covalent bond with A in Formula 1.

The substituents not forming the covalent bond among $R_a$ to $R_f$ may be each independently hydrogen, an alkyl group, an alkoxy group or an aryl group, where at least one is an alkyl group.

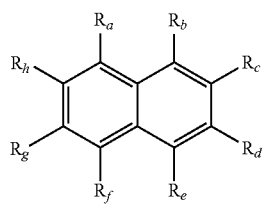

[Formula 3]

When the radical formed by Formula 3 is $Q_1$ in Formula 1, two of $R_a$ to $R_h$ in Formula 3 form a covalent bond, provided that any one of the substituents forming the covalent bond may form a covalent bond with $L_1$ in Formula 1 and another may form a covalent bond with A in Formula 1, and when the radical is $Q_2$ in Formula 1, two of $R_a$ to $R_h$ in Formula 3 form a covalent bond, provided that any one of the substituents forming the covalent bond may form a covalent bond with $L_2$ in Formula 1 and another may form a covalent bond with A in Formula 1.

The substituents not forming the covalent bond among $R_a$ to $R_h$ may be each independently hydrogen, an alkyl group, an alkoxy group or an aryl group, where at least one is an alkyl group.

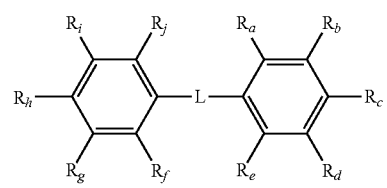

[Formula 4]

In Formula 4, L may be an alkylene group, an alkylidene group, an oxygen atom or a sulfur atom. On the other hand, when the radical formed by Formula 4 is $Q_1$ in Formula 1, two of $R_a$ to $R_h$ in Formula 4 form a covalent bond, provided that any one of the substituents forming the covalent bond may form a covalent bond with $L_1$ in Formula 1 and another may form a covalent bond with A in Formula 1, and when the radical is $Q_2$ in Formula 1, two of $R_a$ to $R_h$ in Formula 4 form a covalent bond, provided that any one of the substituents forming the covalent bond may form a covalent bond with $L_2$ in Formula 1 and another may form a covalent bond with A in Formula 1.

The substituents not forming the covalent bond among $R_a$ to $R_h$ may be each independently hydrogen, an alkyl group, an alkoxy group or an aryl group, where at least one may be an alkyl group.

The number of the alkyl groups with which the aromatic divalent radical is substituted, is not particularly limited and may be, for example, 1 to 12, 1 to 8, 1 to 4, or 1 to 2.

In one example, the aromatic radicals of $Q_1$ and $Q_2$ in Formula 1 may be formed by the aromatic compound of Formula 2 above. In this case, a substituent present in at least ortho, meta or para position on the basis of the substituent forming a covalent bond with A among $R_a$ to $R_f$ in Formula 2, suitably a substituent in the para position may be a radical forming a covalent bond with $L_1$ and/or $L_2$.

Also, in the above structure, a substituent present in at least ortho, meta or para position on the basis of the substituent forming a covalent bond with A among $R_a$ to $R_f$ in Formula 2, suitably at least one of substituents present in the ortho or meta position, or the meta position may be an alkyl group, and for example, both two substitutents present in the meta position may be an alkyl group.

In Formula 1, A is an alkylene group or an alkylidene group, and may be, for example, an alkylene group or an alkylidene group, having 1 to 20 carbon atoms, 1 to 16 carbon atoms, 1 to 12 carbon atoms, 1 to 8 carbon atoms, or 1 to 4 carbon atoms.

In Formula 1, $L_1$ and $L_2$ are an alkylene group, an alkylidene group, an oxygen atom or a sulfur atom, and $L_1$ and $L_2$ may be the same or different from each other. A suitable example of $L_1$ and $L_2$ may include an alkylene group, an alkylidene group or an oxygen atom, and for example, both $L_1$ and $L_2$ may be an oxygen atom, but is not limited thereto.

In Formula 1, $R_1$ to $R_{10}$ are each independently hydrogen, an alkyl group, an alkoxy group, an aryl group or a cyano group, provided that at least two of $R_2$ to $R_4$ are a cyano group and at least two of $R_7$ to $R_9$ are a cyano group. A suitable example of $R_1$ to $R_{10}$ other than the cyano group may include hydrogen, an alkyl group or an alkoxy group; or hydrogen or an alkyl group, but is not limited thereto. In one example, $R_2$, $R_3$, $R_7$ and $R_8$ in Formula 1 may be a cyano group, and the remaining substituents may be each independently hydrogen, an alkyl group, an alkoxy group or an aryl group; hydrogen, an alkyl group or an alkoxy group; or hydrogen or an alkyl group.

The compound of Formula 1 has a structure in which an aromatic radical is substituted with an alkyl group as described above. Accordingly, the compound can exhibit a low processing temperature and an appropriate onset temperature, and a wide process window. In addition, the compound can exhibit excellent heat resistance. In the present application, the term processing temperature may mean a temperature that the compound, and the following polymerizable composition or prepolymer containing it, etc. are present in a processable state. Such a processing temperature may be, for example, a melting temperature (Tp) or a glass transition temperature (Tg).

Accordingly, the compound can provide a polymerizable composition and a prepolymer which have excellent curability, exhibit a suitable processing temperature and a wide process window, and can form a composite having excellent physical properties.

In one example, the processing temperature of the compound may be in a range of 50° C. to 250° C., 80° C. to 200° C., or 90° C. to 150° C. Such a range is advantageous for realizing a polymerizable composition or prepolymer capable of exhibiting appropriate fluidity and processability, securing a wide process window and forming a composite having excellent physical properties.

The compound of Formula 1 can be effectively used in various applications in which so-called phthalonitrile compounds are known to be applicable. For example, the phthalonitrile compound can be effectively used as a raw material or precursor capable of producing a so-called phthalonitrile resin. The compound may exhibit a suitable melting temperature, have excellent reactivity with a curing agent and exhibit a wide process window to be effectively applied to the application. The compound may be used as a precursor of a dye such as a phthalocyanine dye or a precursor or a raw material of a fluorescent brightener, a photographic sensitizer or an acid anhydride, and the like, in addition to the above applications.

The compound of Formula 1 can be synthesized by a known synthesis method of an organic compound. For example, the compound of Formula 1 can be synthesized by a method of reacting an aromatic compound having a phenolic hydroxy group and an aromatic compound having at least two cyano groups (ex. nitro displacement method), and the like. In the field of organic chemistry, the aromatic compounds capable of forming the structure of the compound of Formula 1 are known, and such a compound can be all applied to the production of the above compounds in consideration of the desired structure.

The present application also relates to a use of the compound. As the use of the compound, a raw material or a precursor of a phthalonitrile resin, a phthalocyanine dye, a fluorescent brightener, a photographic sensitizer or an acid anhydride can be exemplified, as described above. As one example of the use, for example, the present application may be directed to a phthalonitrile resin. The phthalonitrile resin may contain a polymerized unit derived from the compound of the Formula 1. In the present application, the term polymerized unit derived from a certain compound may mean a skeleton of a polymer formed by polymerization or curing of the compound.

The phthalonitrile resin may contain 40% or more, 45% or more, 50% or more, 55% or more, 60% or more, 65% or more, 70% or more, 75% or more, 80% or more, 85% or more, or 90% or more of the polymerized unit of the phthalonitrile compound by weight. The polymerized unit of the phthalonitrile compound contained in the phthalonitrile resin in the above ratio may be a polymerized unit of the compound of the Formula 1 or a polymerized unit of a mixture of the compound of the Formula 1 and another phthalonitrile compound. In another example, the ratio may be less than 100%, or 99% or less.

Also, the phthalonitrile resin may further comprise a polymerized unit of other phthalonitrile compounds in addition to the polymerized unit of the compound of Formula 1. In this case, the kind of the phthalonitrile compound capable of being selected and used is not particularly limited and the known compounds known to be useful for forming the phthalonitrile resin and controlling its physical properties can be applied. As an example of such a compound, compounds disclosed in U.S. Pat. Nos. 4,408,035, 5,003,039, 5,003,078, 5,004,801, 5,132,396, 5,139,054, 5,208,318, 5,237,045, 5,292,854, or 5,350,828 can be exemplified, but is not limited thereto.

In the phthalonitrile resin, the polymerized unit of the compound of Formula 1 may be a polymerized unit formed by reaction of the above compound and a curing agent. In this case, the kind of the usable curing agent is not particularly limited as long as it can react with the compound of the Formula 1 to form a polymer, and for example, any compound which is known to be useful for forming the phthalonitrile resin can be used. Such a curing agent is known in various documents including the above-described US patents.

In one example, an amine compound such as an aromatic amine compound or a hydroxy compound can be used as a curing agent. In the present application, the hydroxy compound may mean a compound containing at least one or two hydroxy groups in the molecule. Curing agents capable of curing a phthalonitrile compound to form a resin are variously known, and such curing agents can be applied in most cases in the present application.

One example of the curing agent may include a compound of Formula 5 below.

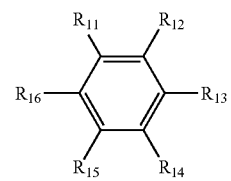

[Formula 5]

In Formula 5, $R_{11}$ to $R_{16}$ are each independently hydrogen, an alkyl group, an alkoxy group, an aryl group, a hydroxy group, an amino group, or a substituent of Formula 6 below, where at least two of $R_{11}$ to $R_{16}$ are a hydroxy group, an amino group or a substituent of Formula 6 below.

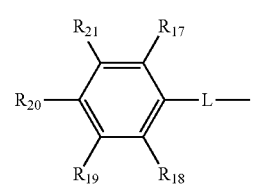

[Formula 6]

In Formula 6, L is a single bond, an oxygen atom, a sulfur atom, an alkylene group or an alkylidene group, and $R_{17}$ to $R_{21}$ are each independently hydrogen, an alkyl group, an alkoxy group, an aryl group, a hydroxy group or an amino group, where at least one of $R_{17}$ to $R_{21}$ is a hydroxy group or an amino group.

In Formula 5, the hydroxy group, the amino group or the substituent of Formula 6, in which 2 or more, for example, 2 to 5, 2 to 4, 2 to 3 or 2 are present, may exist in the ortho, meta or para position to each other.

Also, in Formula 6, the hydroxy group or the amino group, in which at least one, for example, one is present, may exist in the ortho, meta or para position on the basis of L in Formula 6.

The present application also relates to a polymerizable composition. The polymerizable composition may comprise the compound of Formula 1 as described above. The polymerizable composition may further comprise a curing agent together with the compound of Formula 1.

The polymerizable composition may comprise 40% or more, 45% or more, 50% or more, 55% or more, 60% or more, 65% or more, 70% or more, 75% or more, 80% or more, 85% or more, or 90% or more of the phthalonitrile compound by weight. The phthalonitrile compound contained in the polymerizable composition in the above ratio may be the compound of Formula 1 above or a mixture of the compound of Formula 1 above and another phthalonitrile compound. In another example, the ratio may be less than 100%, or 99% or less.

As the curing agent contained in the polymerizable composition, for example, a curing agent such as those already described can be used.

The ratio of the curing agent in the polymerizable composition is not particularly limited. The ratio can be adjusted so that the desired curability can be ensured, for example, in consideration of the ratio or kind of the curable component such as the compound of the Formula 1 contained in the composition. For example, the curing agent may be included in an amount of about 0.02 to 2.5 moles, about 0.02 to 2.0 moles, or about 0.02 to 1.5 moles per mole of the compound of Formula 1 contained in the polymerizable composition. However, the above ratios are only examples of the present application. Usually, if the ratio of the curing agent in the polymerizable composition is high, the process window tends to be narrowed, whereas if the ratio of the curing agent is low, the curability tends to become insufficient, so that the suitable ratio of the curing agent can be selected in consideration of this point.

The polymerizable composition of the present application can exhibit a proper processing temperature and a wide process window, while having excellent curability.

In one example, the processing temperature of the polymerizable composition may be in a range of 50° C. to 250° C., 80° C. to 200° C., or 90° C. to 150° C. In this case, the process window of the polymerizable composition, that is, the absolute value of the difference (Tc–Tp) between the processing temperature (Tp) and the curing temperature (Tc) of the compound of Formula 1 and the curing agent may be 30° C. or more, 50° C. or more, or 100° C. or more. In one example, the curing temperature (Tc) may be higher than the processing temperature (Tp). Such a range may be advantageous, for example, for securing proper processability in the process of producing a composite to be described below, by using the polymerizable composition. Here, although the upper limit of the process window is not particularly limited, for example, the absolute value of the difference (Tc–Tp) between the processing temperature (Tp) and the curing temperature (Tc) may be 400° C., 300° C. or less, or 200° C. or less.

The polymerizable composition may further comprise various additives, including other phthalonitrile compounds and the like, in addition to the compound of the Formula 1. As an example of such an additive, various fillers can be exemplified. The kind of the material that can be used as the filler is not particularly limited, and any known suitable filler may be used depending on the intended uses. As the exemplary filler, a metal material, a ceramic material, glass, a metal oxide, a metal nitride or a carbon-based material, and the like can be exemplified, but is not limited thereto. Furthermore, the type of the filler is not particularly limited as well and may be various forms, such as fibrous materials such as aramid fibers, glass fibers or ceramic fibers, or woven fabrics, nonwoven fabrics, strings or cords, formed by the materials, particulates comprising nanoparticles, polygons or other amorphous forms. Here, as the carbon-based materials, graphite, graphene or carbon nanotubes, and the like, or derivatives or isomers such as oxides thereof, and the like can be exemplified. However, the components that the polymerizable composition may further comprise are not limited to the above, and various monomers known to be applicable to the production of so-called engineering plastics such as polyimide, polyamide or polystyrene, or other additives may also be included without limitation, depending on the purpose.

The present application also relates to a prepolymer formed by reaction of the polymerizable composition, that is, the polymerizable composition comprising the compound of Formula 1 and a curing agent.

In the present application, the term prepolymer state may mean a state where the compound of Formula 1 and the curing agent in the polymerizable composition are in a state polymerized in a certain degree (for example, a state that polymerization of a so-called stage A or B step occurs), without reaching a completely polymerized state, and exhibit an appropriate fluidity, for example, allow to process a composite to be described below. In one example, the prepolymer state is a state where polymerization of the polymerizable composition proceeds to some extent and may be a solid state such as a dust or powder at room temperature of the composition. In the present application, the term room temperature is a natural temperature that a temperature is not increased or decreased and may mean, for example, a temperature of about 10° C. to 30° C., about 15° C. to 30° C., about 20° C. to 30° C., 25° C. or 23° C. or so.

The prepolymer may also exhibit excellent curability, an appropriate processing temperature and a wide process window.

For example, the processing temperature of the prepolymer may be in a range of 50° C. to 250° C., 80° C. to 200° C., or 90° C. to 150° C. In this case, the process window of the prepolymer, that is, the absolute value of the difference (Tc–Tp) between the processing temperature (Tp) and the curing temperature (Tc) of the prepolymer may be 30° C. or more, 50° C. or more, or 100° C. or more. In one example, the curing temperature (Tc) may be higher than the processing temperature (Tp). Such a range may be advantageous, for example, for securing proper processability in the process of producing a composite to be described below, by using the prepolymer. Here, although the upper limit of the process window is not particularly limited, for example, the absolute value of the difference (Tc–Tp) between the processing temperature (Tp) and the curing temperature (Tc) may be 400° C. or less, 300° C. or less, or 200° C. or less.

The prepolymer may further comprise any known additives in addition to the above components. As the example of such an additive, the above-described fillers and the like can be exemplified, but is not limited thereto.

The present application also relates to a composite. The composite may comprise the above-described phthalonitrile resin and filler. As described above, it is possible to achieve excellent curability, an appropriate processing temperature and a wide process window through the compound of the Formula 1 of the present application, and accordingly, a so-called reinforced resin composite (reinforced polymer composite) with excellent physical properties comprising various fillers can be easily formed. The composite thus formed may comprise the phthalonitrile resin and filler and may be applied to, for example, various applications, including durables such as automobiles, airplanes or ships, and the like.

The kind of the filler is not particularly limited and may be suitably selected in consideration of the intended use. A specific example of the filler is as described above, but is not limited thereto.

Also, the ratio of the filler is not particularly limited and may be set in an appropriate range depending on the intended use.

The present application also relates to a precursor for producing the composite, wherein the precursor may comprise, for example, the polymerizable composition and the filler as described above, or the prepolymer and the filler as described above.

The composite can be prepared in a known manner using the precursor. For example, the composite can be formed by curing the precursor.

In one example, the precursor may be prepared by blending the polymerizable composition, which is prepared by compounding the compound of Formula 1 described above with a curing agent in a molten state, or the prepolymer, with the filler in a state molten by heating or the like. For example, the above-described composite can be prepared by molding the precursor thus produced into a desired shape and then curing it. The polymerizable composition or prepolymer has an appropriate processing temperature and a wide process temperature together with excellent curability, so that molding and curing can be efficiently performed in the above process.

In the above processes, the method for forming the prepolymer or the like, the method for producing the composite by compounding such a prepolymer with the filler, and processing and curing it, and the like may be carried out according to known methods.

The present application may be also directed to a precursor of a phthalocyanine dye, a precursor of a fluorescent brightener or a precursor of a photographic sensitizer, comprising the compound, or an acid anhydride derived from the compound. The method for forming the precursor or the method for producing the acid anhydride, using the compound, is not particularly limited and all known methods capable of producing the precursor or acid anhydride using phthalonitrile compounds can be applied.

ADVANTAGEOUS EFFECTS

The present application may provide a phthalonitrile compound and a use thereof. The phthalonitrile compound has a novel structure and can exhibit excellent effects in known applications to which the phthalonitrile compound can be applied. As the use of such a phthalonitrile compound, raw materials or precursors such as so-called phthalonitrile resins, phthalocyanine dyes, fluorescent brighteners, photographic sensitizers or acid anhydrides can be exemplified.

BRIEF DESCRIPTION OF DRAWINGS

FIG. 1 shows NMR results of the compound of Preparation Example 1.
FIG. 2 shows NMR results of the compound of Preparation Example 2.
FIG. 3 shows NMR results of the compound of Preparation Example 3.

MODE FOR INVENTION

The phthalonitrile resins of the present application and the like will be specifically described by way of Examples and Comparative Examples, but the scope of the resins and the like is not limited to the following examples.

1. NMR, DSC and TGA Analyses

The NMR analysis was carried out using an equipment (Agilent 500 MHz NMR device) according to the manufacturer's manual (solvent used: DMSO (d6) (dimethylsulfoxide-d6)).

In addition, for the DSC (differential scanning calorimetry) analysis, it was measured in $N_2$ flow atmosphere while raising the temperature from 35° C. to 450° C. at a rate of about 10° C./min using a Q20 system from TA Instrument.

Furthermore, for the TGA (thermogravimetric analysis) analysis, the compound was measured in $N_2$ flow atmosphere while raising the temperature from 25° C. to 800° C. at a rate of about 10° C./min and the polymerizalbe composition was measured in $N_2$ flow atmosphere while raising the temperature from 25° C. to 900° C. at a rate of about 10° C./min, using a TGA e850 from Mettler-Toledo.

Preparation Example 1

The compound of Formula A below was synthesized by a nitro displacement reaction. 41.0 g of bis(4-hydroxy-3,5-dimethylphenyl)methane (CAS No. 5384-21-4) and 150 mL of DMF (dimethyl formamide) were placed in a 500 mL flask (3 neck round-bottom flask) and stirred at room temperature. To the mixture, 55.4 g of 4-nitrophthalonitrile was added and dissolved by further adding 50 g of DMF thereto and stirring the mixture. 66.3 g of potassium carbonate was added thereto together with 50 g of DMF, and the temperature was raised to 85° C. with stirring. After reaction for about 5 hours, followed by cooling to room temperature, the cooled reaction solution was poured into 0.2N hydrochloric acid aqueous solution to be neutralized and precipitated, and the precipitate was filtered and then washed with water. The filtered product was dried in a vacuum oven at 100° C. for one day to remove water and residual solvent, and the desired compound was obtained. The NMR analysis results for the prepared compound were shown in FIG. 1.

[Formula A]

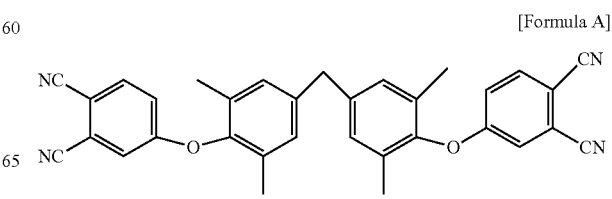

Preparation Example 2

The compound of Formula B below was also synthesized by a nitro displacement reaction. 27.9 g of 4,4'-dihydroxybiphenyl and 100 mL of DMF (dimethyl formamide) were placed in a 500 mL flask (3 neck round-bottom flask) and stirred at room temperature. To the mixture, 51.9 g of 4-nitrophthalonitrile was added and dissolved by further adding 50 g of DMF thereto and stirring the mixture. 62.2 g of potassium carbonate was added thereto together with 50 g of DMF, and the temperature was raised to 85° C. with stirring. After reaction for about 5 hours, followed by cooling to room temperature, the cooled reaction solution was poured into 0.2N hydrochloric acid aqueous solution to be neutralized and precipitated, and the precipitate was filtered and then washed with water. The filtered product was dried in a vacuum oven at 100° C. for one day to remove water and residual solvent, and the desired compound was obtained. The NMR analysis results for the prepared compound were shown in FIG. 2.

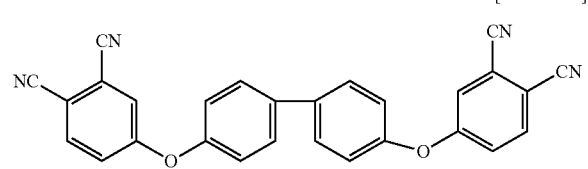

[Formula B]

Preparation Example 3

The compound of Formula C below was also synthesized by a nitro displacement reaction. 0.4 g of 2,2-bis(3-amino-4-hydroxyphenyl)hexafluoropropane and 150 mL of DMF (dimethyl formamide) were placed in a 500 mL flask (3 neck round-bottom flask) and stirred at room temperature. To the mixture, 51.9 g of 4-nitrophthalonitrile was added and dissolved by further adding 50 g of DMF thereto and stirring the mixture. 62.2 g of potassium carbonate was added thereto together with 50 g of DMF, and the temperature was raised to 85° C. with stirring. After reaction for about 5 hours, followed by cooling to room temperature, the cooled reaction solution was poured into 0.2N hydrochloric acid aqueous solution to be neutralized and precipitated, and the precipitate was filtered and then washed with water. The filtered product was dried in a vacuum oven at 100° C. for one day to remove water and residual solvent, and the desired compound was obtained. The NMR analysis results for the prepared compound were shown in FIG. 3.

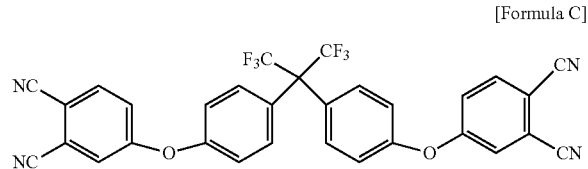

[Formula C]

Preparation Example 4

As the compound of Formula D below (m-APB), a product from TCI was purchased and used without further purification.

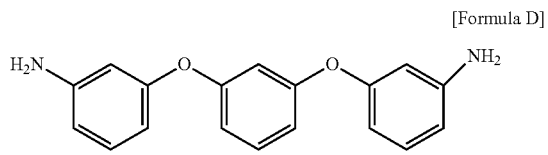

[Formula D]

The physical properties such as the melting temperature (Tm) of the compounds of Preparation Examples 1 to 3 are summarized in Table 1 below.

TABLE 1

|  | Tm (unit: ° C.) | Residue at 800° C. (unit: %) |
| --- | --- | --- |
| Preparation Example 1 | 193 | 73 |
| Preparation Example 2 | 235 | 1.1 |
| Preparation Example 3 | 183 | 0.5 |

Example 1

A polymerizable composition was prepared by compounding a curing agent (compound of Preparation Example 4) to 4 g of the compound of Formula A synthesized in Preparation Example 1 so that 12 moles of the curing agent was present per mole of the compound of Formula A. The mixture can be melted at about 200° C. and rapidly cooled for 5 minutes to prepare a precursor (prepreg).

Comparative Example 1

A polymerizable composition was prepared in the same manner as in Example 1, except that the compound of Formula B in Preparation Example 2 was used instead of the compound of Formula A synthesized in Preparation Example 1, and the physical properties were evaluated.

Comparative Example 2

A polymerizable composition was prepared in the same manner as in Example 1, except that the compound of Formula C in Preparation Example 3 was used instead of the compound of Formula A synthesized in Preparation Example 1, and the physical properties were evaluated.

The physical properties measured for the results of Example 1 and Comparative Examples 1 and 2 above are summarized in Table 2 below.

TABLE 2

|  | Tm (unit: ° C.) | Exothermal Onset Temperature (unit: ° C.) | Process Window (unit: ° C.) | Residue at 900° C. (unit: %) |
| --- | --- | --- | --- | --- |
| Example 1 | 186 | 296 | 110 | 75 |
| C. Example 1 | 233 | 263 | 30 | 64 |
| C. Example 2 | 230 | 280 | 70 | 52 |

(C. Example: Comparative Example)

From the results of Tables 1 and 2, it can be confirmed that the compound of the specific formula of the present application exhibits a low processing temperature (melting temperature, Tm) and an appropriate onset temperature, and a wide process window, and it can be seen that the compound has excellent heat resistance.

The invention claimed is:

1. A phthalonitrile resin comprising a polymerized unit derived from a compound of Formula 1 below:

[Formula 1]

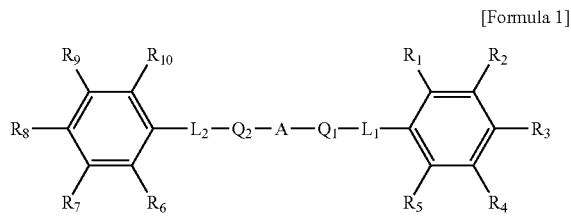

wherein, A is an alkylene group or an alkylidene group, having 1 to 20 carbon atoms, $Q_1$ and $Q_2$ are an aromatic divalent radical substituted with at least one alkyl group, $L_1$ and $L_2$ are each independently an alkylene group, an alkylidene group, an oxygen atom or a sulfur atom, $R_1$ to $R_{10}$ are each independently hydrogen, an alkyl group, an alkoxy group, an aryl group or a cyano group, provided that at least two of $R_1$ to $R_5$ are a cyano group and at least two of $R_6$ to $R_{10}$ are a cyano group.

2. The phthalonitrile resin according to claim 1, wherein $Q_1$ and $Q_2$ in Formula 1 are each independently a radical derived from an aromatic compound of Formula 2 below:

[Formula 2]

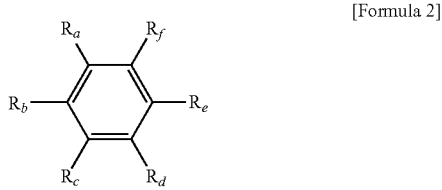

wherein, $R_a$ to $R_f$ are each independently hydrogen, an alkyl group, an alkoxy group or an aryl group, where two of $R_a$ to $R_f$ form a covalent bond, provided that any one of two forming said covalent bond forms a covalent bond with $L_1$ or $L_2$ in Formula 1 and the other forms a covalent bond with A in Formula 1, and at least one of the substituents not forming said covalent bond among $R_a$ to $R_f$ is an alkyl group.

3. The phthalonitrile resin according to claim 2, wherein the substituent present in the para position on the basis of the substituent forming a covalent bond with A in Formula 1 among $R_a$ to $R_f$ in Formula 2 forms a covalent bond with $L_1$ or $L_2$ in Formula 1.

4. The phthalonitrile resin according to claim 3, wherein at least one of the substituents present in the ortho or meta position on the basis of the substituent forming a covalent bond with A in Formula 1 among $R_a$ to $R_f$ in Formula 2 is an alkyl group.

5. The phthalonitrile resin according to claim 3, wherein at least one of the substituents present in the meta position on the basis of the substituent forming a covalent bond with A in Formula 1 among $R_a$ to $R_f$ in Formula 2 is an alkyl group.

6. The phthalonitrile resin according to claim 3, wherein two substituents present in the meta position on the basis of the substituent forming a covalent bond with A in Formula 1 among $R_a$ to $R_f$ in Formula 2 are an alkyl group.

7. The phthalonitrile resin according to claim 1, wherein $L_1$ and $L_2$ are each independently an alkylene group, an alkylidene group or an oxygen atom.

8. The phthalonitrile resin according to claim 1, wherein in Formula 1, any two of $R_2$ to $R_4$ are a cyano group and any two of $R_7$ to $R_9$ are a cyano group.

9. A polymerizable composition comprising the compound as defined in claim 1 and a curing agent.

10. A prepolymer which is reaction product of the polymerizable composition of claim 9.

11. A composite comprising the phthalonitrile resin of claim 1 and a filler.

12. The composite according to claim 11, wherein the filler is a metal material, a ceramic material, glass, a metal oxide, a metal nitride or a carbon-based material.

13. A precursor comprising the polymerizable composition of claim 9; and a filler.

14. A method for producing a composite comprising a step of curing the precursor of claim 13.

15. A precursor comprising the prepolymer of claim 10; and a filler.

* * * * *